(12) United States Patent
Lindner et al.

(10) Patent No.: US 9,173,990 B2
(45) Date of Patent: Nov. 3, 2015

(54) SYSTEM FOR BLOOD SEPARATION WITH REPLACEMENT FLUID APPARATUS AND METHOD

(75) Inventors: John R. Lindner, Morrison, CO (US); William Sweat, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 683 days.

(21) Appl. No.: 13/569,673

(22) Filed: Aug. 8, 2012

(65) Prior Publication Data

US 2013/0040797 A1   Feb. 14, 2013

Related U.S. Application Data

(60) Provisional application No. 61/522,988, filed on Aug. 12, 2011.

(51) Int. Cl.
*A61M 37/00* (2006.01)
*A61M 1/38* (2006.01)
*A61M 1/36* (2006.01)

(52) U.S. Cl.
CPC ............... *A61M 1/38* (2013.01); *A61M 1/3693* (2013.01); *A61M 1/3695* (2014.02); *A61M 1/3696* (2014.02)

(58) Field of Classification Search
CPC . A61M 1/3696; A61M 1/3441; A61M 1/342; A61M 1/3693; A61M 1/38
See application file for complete search history.

(56) References Cited

U.S. PATENT DOCUMENTS

| | | |
|---|---|---|
| 5,795,317 A | 8/1998 | Brierton et al. |
| 6,053,856 A | 4/2000 | Hlavinka |
| 6,234,989 B1 | 5/2001 | Brierton et al. |
| 6,280,406 B1 | 8/2001 | Dolecek et al. |
| 6,361,518 B1 | 3/2002 | Brierton et al. |
| 6,730,055 B2 | 5/2004 | Bainbridge et al. |
| 6,764,460 B2 | 7/2004 | Dolecek et al. |
| 6,808,503 B2 * | 10/2004 | Farrell et al. .................. 604/6.01 |
| 7,201,848 B2 | 4/2007 | Antwiler et al. |
| 7,588,692 B2 | 9/2009 | Antwiler et al. |
| 7,935,043 B2 | 5/2011 | Fender |
| 8,123,713 B2 | 2/2012 | Felt et al. |
| 2003/0211927 A1 | 11/2003 | Cantu et al. |

OTHER PUBLICATIONS

"International Search Report and Written Opinion", PCT/US2012049958, Oct. 26, 2012.

\* cited by examiner

*Primary Examiner* — Leslie Deak
(74) *Attorney, Agent, or Firm* — John R. Merkling; Elizabeth J. Reagan; René A. Pereyra (57) ABSTRACT

A method is provided in a centrifugal blood processing system for adding replacement fluid without a dedicated peristaltic pump to blood components being returned to the donor. A disposable blood processing set for use in the method comprises a hermetically sealed set of blood bags, connecting tubes, needles or connectors, and supporting structures with a replacement fluid line coupled directly to a return reservoir without contact with an intervening pump.

9 Claims, 4 Drawing Sheets

SYSTEM FOR BLOOD SEPARATION WITH REPLACEMENT FLUID APPARATUS AND METHOD

CROSS-REFERENCE TO RELATED APPLICATIONS

This application claims the priority of U.S. Provisional Application No. 61/522,988, currently pending, filed on Aug. 12, 2011.

BACKGROUND OF INVENTION

Blood collection and blood processing play important roles in the worldwide health care system. In conventional large scale blood collection, blood is removed from a donor or patient (hereinafter "donor"), separated into its various blood components via centrifugation, filtration, or elutriation and stored in sterile containers for future infusion into a patient for therapeutic use. The separated blood components typically include fractions comprising red blood cells, white blood cells, platelets, and plasma. Separation of blood into its components can be performed continuously during collection or can be performed subsequent to collection in batches, particularly with respect to the processing of whole blood samples. Separation of blood into its various components under highly sterile conditions is critical to many therapeutic applications.

Apheresis blood collection techniques have been adopted in many large scale blood collection centers wherein a selected component of blood is collected and the balance of the blood is returned to the donor during collection. In apheresis systems, blood is removed from a donor and immediately separated into its components by on-line blood processing methods. Typically, on-line blood processing is provided by density centrifugation, filtration, or diffusion-based separation techniques. One or more of the separated blood components are collected and stored in sterile containers, while the remaining blood components are directly re-circulated to the donor. An advantage of this method is that it allows more frequent donation from an individual donor because only a selected blood component is collected and purified. For example, a donor undergoing plateletpheresis, whereby platelets are collected and the non-platelet blood components are returned to the donor, may donate blood as often as once every fourteen days.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation.

Both conventional blood collection and apheresis systems typically employ differential centrifugation methods for separating blood into its various blood components. In differential centrifugation, blood is circulated through a sterile blood processing vessel which is rotated at high rotational speeds about a central rotation axis. Rotation of the blood processing vessel creates a centrifugal force directed along rotating axes of separation oriented perpendicular to the central rotation axis of the centrifuge. The centrifugal force generated upon rotation separates particles suspended in the blood sample into discrete fractions having different densities. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. Descriptions of blood centrifugation devices are provided in U.S. Pat. Nos. 5,653,887 and 7,033,512.

When a blood component is removed it is often advisable to replace the volume of the removed component when the remaining portions of the blood are returned to the donor. This maintains the fluid volume in the cardiovascular system of the donor. It is an object of this disclosure to provide a safe and accurate means and method for providing a controlled quantity of replacement fluid.

A centrifugal blood component separation apparatus has been described in commonly assigned U.S. Pat. No. 7,605,388, for instance. As described in U.S. Pat. No. 7,605,388, an optical cell may be configured such that white blood cells can be extracted through a first extraction port, plasma and/or platelets can be extracted through second extraction port, and red blood cells can be extracted through third extraction port. As also mentioned in U.S. Pat. No. 7,605,388 (but not shown), optical cells of a blood separation vessel can include one or more dams positioned proximate to the extraction ports to facilitate selective extraction of separated blood components having reduced impurities arising from adjacent components.

SUMMARY OF THE INVENTION

This invention provides methods, devices and device components for improving the processing of fluids comprising fluid components, such as blood, components of blood and fluids derived from blood. The apparatus comprises a centrifugal blood separator for apheresis, that is, for a blood separator that withdraws whole blood from a donor, separates the blood into components, collects or removes at least one component, and returns other components to the donor. A plurality of peristaltic pumps controls the flow of whole blood, blood components and certain other fluids, such as anti-coagulant (AC). In the present apparatus and method, it is desired to control more fluid flows than there are available pumps. Consequently, a method is provided for adding replacement fluid without a dedicated peristaltic pump to blood components being returned to the donor. A disposable blood processing set comprises a hermetically sealed set of blood bags, connecting tubes, needles or connectors, and supporting structures that can be mounted on the centrifugal blood separator and in which the whole blood is separated into components.

It is intended, therefore, to provide a disposable blood processing set for use on a centrifugal blood processing device, the disposable set comprising: a blood separation chamber adapted to be mounted on a rotor of the centrifugal blood processing device; a blood inlet line adapted to be coupled to a blood donor and to an inlet pump on said centrifugal blood processing device; an anti-coagulant line in fluid communication with said inlet line, said anti-coagulant line being adapted to be fluidly coupled to a supply of anti-coagulant and being further adapted to be coupled to an anti-coagulant pump on said centrifugal blood processing device; a reservoir adapted to be coupled to at least one sensor for detecting a level of fluid in said reservoir; a return line in fluid communication with said reservoir, the return line being adapted to be coupled to the blood donor and to a return pump on said centrifugal blood processing device; a red blood cell line in fluid communication with said blood separation chamber and said reservoir; a collect line in fluid communication with the blood separation chamber and in selective communication with the reservoir and a collect bag, the collect line being adapted to be coupled to a collect pump; a plasma line in fluid communication with the blood separation chamber and with the reservoir, said plasma line being adapted to be coupled to a plasma pump; and a replacement fluid line in fluid communication with the reservoir and adapted to be placed in fluid communication with a source of replacement fluid.

It is also desired to provide a centrifugal blood separator programmed for and having means to add a controlled amount of replacement fluid to blood components being returned to a donor without a peristaltic pump dedicated to controlling the flow volume of the replacement fluid.

It is intended that a method for controlling a centrifugal blood separator provide a controlled amount of blood replacement fluid to a blood donor. The method may comprise removing whole blood from a donor through an inlet line; providing anti-coagulant to whole blood in the inlet line; measuring the flow of whole blood and anti-coagulant in the inlet line; separating the whole blood and the anti-coagulant into a plurality of blood components in a separation chamber; flowing red blood cells from the separation chamber into a reservoir; flowing a first blood component from the separation chamber into the reservoir; measuring the flow of the first blood component into the reservoir; removing a second blood component from the separation chamber; measuring the flow of the second component; selectively flowing at least part of the second component into the reservoir; selectively flowing replacement fluid into the reservoir; periodically flowing contents of the reservoir into a return line; measuring the flow of the contents; and determining a quantity of replacement fluid delivered to the donor from the measured inlet line flow, first blood component flow, collect flow and return flow. The flow of replacement fluid is not measured directly.

In another aspect of the method, selectively flowing replacement fluid into the reservoir may comprise allowing the replacement fluid to flow without mechanical assistance.

Measuring the flow of contents of the reservoir may comprise counting revolutions of a peristaltic pump.

In as much as an accurate measurement of the blood components and replacement fluid being infused into a donor is needed, the method may comprise flowing the contents of said reservoir during a first period of time when replacement fluid is not flowed into the reservoir and flowing the contents of the reservoir during a second period of time when replacement fluid is flowed into the reservoir. The first and second periods of time may alternate and the first period may be at least as long as the second period.

Each period may comprise at least one cycle, each cycle comprising a discrete step of removing whole blood and a discrete step of flowing contents of the reservoir into the return line. The ratio of the number of cycles in the first period to the number of cycles in the second period may be as frequent as 1 to 1 (that is, flowing replacement fluid during every second cycle).

These and other features and advantages will be apparent from the following description, drawings and claims.

DETAILED DESCRIPTION

To describe the present invention, reference will now be made to the accompanying drawings. The present invention may be used with a blood processing apparatus such as a SPECTRA OPTIA® blood component centrifuge manufactured by Terumo BCT, Inc. (formerly known as CaridianBCT, Inc.), or a TRIMA® or TRIMA ACCEL® blood component centrifuge also manufactured by Terumo BCT, Inc. The invention may also be used with other blood component centrifuges. The above-named centrifuges incorporate a one-omega/two-omega seal-less tubing connection as disclosed in U.S. Pat. No. 4,425,112 to provide a continuous flow of blood to and from the rotor of an operating centrifuge without requiring a rotating seal.

Figure 1:
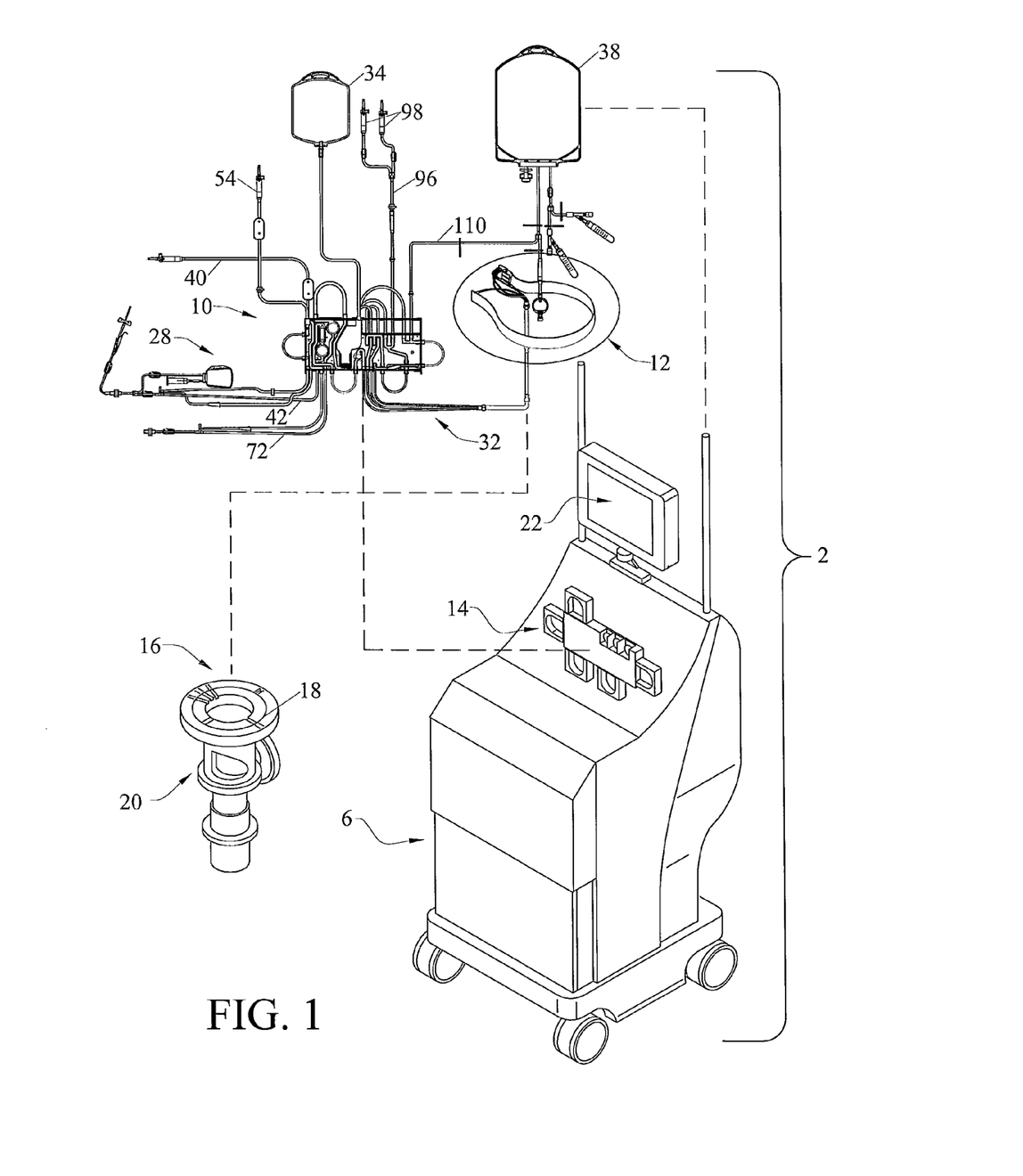
FIG. 1 is a schematic view of one embodiment of an apheresis system, which can be used in or with the present invention.

A blood-separation apheresis system 2 is schematically illustrated in FIG. 1. The blood separation system 2 provides for a continuous blood component separation process. Generally, whole blood is withdrawn from a donor and is provided to a blood component separation device 6 where the blood is separated into various components and at least one of these blood components is collected from the device 6. One or more of the separated blood components may be either collected for subsequent use or returned to the donor. In the blood apheresis system 2, blood is withdrawn from the donor and directed through a bag and tubing set 8, which includes an extracorporeal tubing circuit 10 and a blood processing vessel 12, which together define a closed, sterile, disposable system. The set 8 is adapted to be mounted in the blood component separation device 6. The separation device 6 includes a pump/valve/sensor assembly 14, which interfaces with the extracorporeal tubing circuit 10, and a centrifuge assembly 16, which interfaces with the blood processing vessel 12.

The centrifuge assembly 16 may include a channel 18 in a rotatable rotor assembly 20, which rotor assembly provides the centrifugal forces (sometimes referred to as a "gravitational field") required to separate blood into its various blood component types by centrifugation. The blood processing vessel 12 may then be fitted within the channel 18. Blood can flow substantially continuously from the donor, through the extracorporeal tubing circuit 10, and into the rotating blood processing vessel 12. Within the blood processing vessel 12, blood may be separated into various blood component types and at least one of these blood component types (e.g., white blood cells, platelets, plasma, or red blood cells) may be removed from the blood processing vessel 12. Blood components that are not being retained for collection or for therapeutic treatment (e.g., platelets and/or plasma) are also removed from the blood processing vessel 12 and returned to the donor via the extracorporeal tubing circuit 10. Various alternative apheresis systems (not shown) may also be used, including batch processing systems (non-continuous inflow of whole blood and/or non-continuous outflow of separated blood components) or smaller scale batch or continuous RBC/plasma separation systems, whether or not blood components may be returned to the donor.

Operation of the blood component separation device 6 is controlled by one or more processors included therein, and may advantageously comprise a plurality of embedded computer processors to accommodate interface with PC user facilities (e.g., CD ROM, modem, audio, networking and other capabilities). In order to assist the operator of the apheresis system 2 with various aspects of its operation, the blood component separation device 6 includes a graphical interface 22 with an interactive touch screen.

Figure 2:
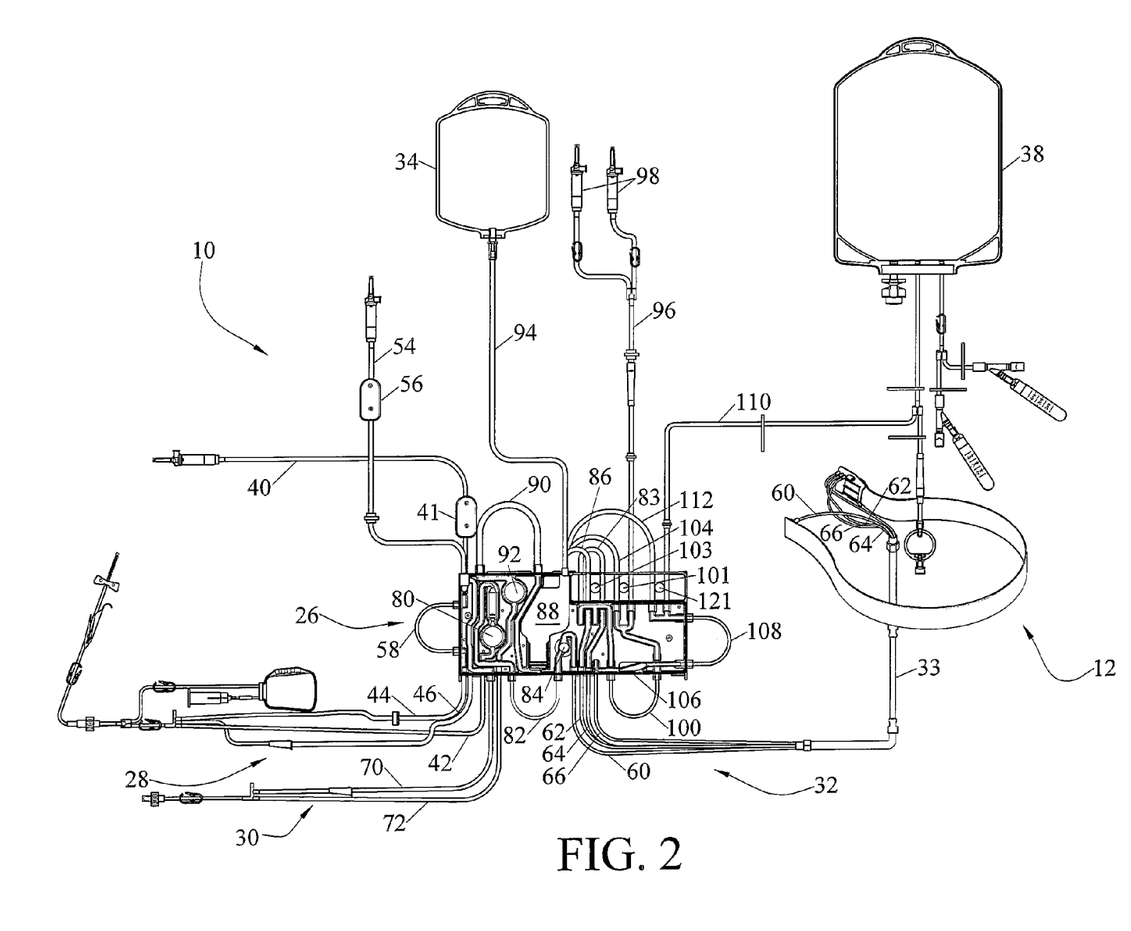
FIG. 2 illustrates a tubing and bag set including an extracorporeal tubing circuit, a cassette assembly, collection bag assembly, a blood processing vessel, and a cell separation chamber for use in or with the system of FIG. 1.

An extracorporeal tubing circuit 10, shown in FIG. 2, may include a cassette 26 and a number of tubing/collection assemblies 28, 30, 34, 38 and 40. A blood removal tubing assembly 28 provides a needle interface for withdrawing blood from a donor to the remainder of the tubing circuit 10 and a return tubing assembly 30 provides an interface for returning blood components and other fluids to the donor. A double needle configuration is shown, but a single needle interface may also be used (a detachable needle is not shown). Three lines 42, 44, 46 are provided in blood removal tubing assembly 28 for blood removal (line 42), saline prime (line 46), and anti-coagulant (line 44). A cassette 26 is connected between the tubing assembly 28, which connects to the donor, and blood inlet/blood component tubing line sub-assembly 32, which provides the interface between cassette 26 and blood processing vessel 12. The cassette 26 orients tubing segments in predetermined spaced relationships within the cassette 26 for ultimate engagement with valve members and sensors on apheresis device 6. Such valves will, when activated, control flow through loops and tubing.

The tubing line sub-assembly 32 comprises four lines 60, 62, 64, and 66, shown in FIG. 2, for transport of blood and components to and from the processing vessel 12. The four lines are encased in a sheath 33 that allows the one omega-two omega motion described in U.S. Pat. No. 4,425,112. An anti-coagulant tubing assembly 40, a vent bag 34, and a white blood cell collection bag 38 are also interconnected with cassette 26. Optionally, a red blood cell collection assembly or a plasma collection assembly might also be provided, as is known in the art. The principle object of the specific embodiment described herein is to withdraw an intermediate density blood component (such as white blood cells or granulocytes) while returning both red blood cells and plasma to the donor. It is apparent that either red blood cells or plasma could also be collected. The extracorporeal tubing circuit 10 and blood processing vessel 12 are pre-connected to form a closed, sterilized, disposable assembly for a single use.

When the tubing circuit 10 has been mounted on the blood component separation device 6, saline solution primes the tubing circuit through a line 54 and filter 56 (see FIG. 2). Saline solution flows through an internal passageway in the cassette 26 and through the line 44 to the distal end of the blood removal assembly 28. Saline can then flow up a blood withdrawal line 42 into the other tubes and passageways of the circuit 10 in preparation for blood processing. Saline solution also flows through a saline line 70 to the distal end of the blood return assembly. In the event of an interruption in a blood separation procedure, clamps on the lines 44, 70 may be opened to allow saline solution to dilute the fluids at the distal ends of the removal assembly 28 and the return assembly 30. A supply or bag (not shown) of anticoagulant can then be connected to a distal end of the anticoagulant tubing assembly 40. Anticoagulant solution flows past a filter 41 and a first pump loop 58 through the anticoagulant line 44 to the distal end of the blood removal assembly 28. The pump loop 58 and other pump loops described herein couple with peristaltic pumps on the blood processing device 6 in a known manner. The device 6 controls the direction and rate of flow of the fluids described herein by controlling the speed and direction of the peristaltic pumps and the position of various valves. The blood removal line 42 conducts blood into the cassette 26, where the blood passes a first pressure sensor 80 and a second pump loop 82. A second pressure sensor 84, between second pump loop 82 with its associated pump and blood inflow line 60 to the blood processing vessel 12, senses the fluid pressure effective at an inlet to the blood processing vessel 12.

Emanating from blood processing vessel 12 is an RBC outlet tubing line 62 of the blood inlet/blood component tubing assembly 32. The outlet tubing line 62 connects to an external RBC valve loop 86 to a return reservoir 88. The return reservoir 88 contacts sensors on the device 6 that detect low and high fluid levels within the return reservoir 88. The device 6 keeps the fluid in the reservoir between these two levels by controlling flow out of the reservoir past a return pump loop 90 and a return pressure sensor 92. Because the fluid level in the reservoir 88 is constantly rising and falling, a vent bag 34 connects to the reservoir 88 through a vent tube 94. Air can flow between the reservoir 88 and the vent bag 34 in a sterile manner. Fluid flows into a return tube 72 in the blood return assembly 30. If desired, red blood cells could be withdrawn through an auxiliary line (not shown) and collected in a collection bag (not shown).

Plasma may also be withdrawn from the blood processing vessel 12 through plasma line 64, which is coupled to a plasma valve loop 83. The plasma valve loop 83 passes a valve 103 that allows the device 6 to close or open flow of plasma. Plasma may flow past the valve 103 to pump loop 100 and connecting loop or line 104 into reservoir 88. A valve 101 selectively allows replacement fluid to enter connecting loop or line 104 and flow into the reservoir 88 from an auxiliary line 96. A bag or bags containing replacement fluid (not shown) may be connected to one or more spikes or Luer connectors 98 on the auxiliary line 96, allowing replacement fluid to pass through the return loop 104 into the reservoir 88. Blood components and replacement fluid are then returned to the donor as will be described below.

White blood cells, platelets or granulocytes flow out of the blood processing vessel 12 through a cell line 66. In the cassette 26, the fluid from the cell line 66 passes a red-green photo sensor 106, which may be used to control periodic flushing of selected cells out of the blood processing vessel 12 into the collect bag 38. The selected cells flow through a pump loop or line 108, which engages a peristaltic pump on the separation device 6. The pump loop 108 connects to a valved passageway in the cassette 26. The blood processing device 6 can control a valve 121 to direct white blood cells or other selected cells either into a collect tube 110 and thence into the collect bag 38, or into a connection loop or line 112 and thence into the reservoir 88. Excess white blood cells in the reservoir 88 may be returned to the donor in the same way as red blood cells and plasma, as described above.

During a blood removal, whole blood will be passed from a donor into tubing line 42 of blood removal tubing assembly 28. The blood is pumped by the device 6 via pump loop 82, to the blood processing vessel 12, via the cassette 26 and line 60 of the blood inlet/blood component tubing assembly 32. After separation processing in vessel 12, uncollected blood components are transferred from the processing vessel 12 to and through cassette 26 and into reservoir 88 of cassette 26, which is filled up to a predetermined level. The blood component separation device 6 may initiate a blood return submode wherein components may be returned to the donor through return line 72. The cycle between blood removal and blood return submodes will continue until a predetermined amount of blood components have been collected or removed or until the procedure is terminated by the operator because of elapsed time, volume of blood processed or for other conditions.

Figure 3:
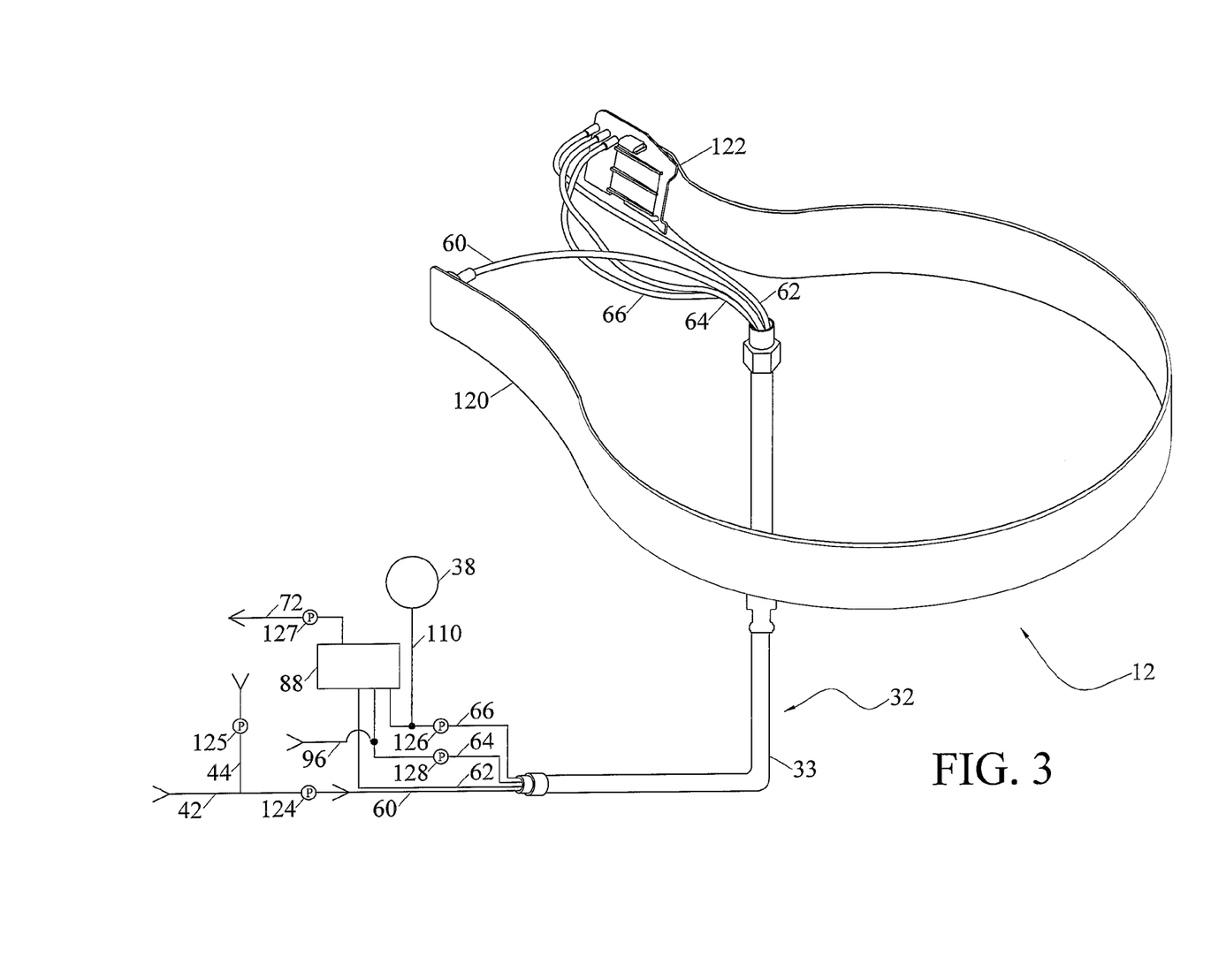
FIG. 3 is a perspective view of a blood processing vessel.

FIG. 3 schematically illustrates the blood processing vessel 12. The blood processing vessel 12 has a generally annular flow path and includes an inlet portion 120 and an outlet portion 122. The inflow tube 60 connects to the inlet portion 120 for conveying a fluid to be separated, such as whole blood, into the blood processing vessel 12. During a separation procedure, substances entering the inlet portion 120 flow around the vessel 12 and stratify according to differences in density in response to rotation of the centrifuge assembly 16. The outlet portion 122 includes outlets for the RBC line 62, the plasma line 66, and buffy coat or white blood cell line 64 for removing separated substances from the blood processing vessel 12. Each of the components separated in the vessel 12 is collected and removed in only one area of the vessel 12, namely the outlet portion 122.

As schematically shown in FIG. 3, a plurality of pumps 124, 125, 126, 127, and 128 are provided for adding and removing substances to and from the blood processing vessel 12. An inflow pump 124 is coupled to the inflow line 60 at pump loop 82 (FIG. 2) to supply the substance to be separated, such as whole blood, to the inlet portion 120. Similarly, an anti-coagulant (AC) pump 125 engages line 44 at loop 58 (FIG. 2) to provide a controlled amount of anti-coagulant to the incoming whole blood. The total volume of fluid entering the separation vessel 12 is known from the size of the loop 82 and the revolutions of the peristaltic inflow pump 124.

A first collection pump 126 is coupled at loop 100 to the collect line 66. As described above, the fluid being removed (white cells, granulocytes, etc.) may be selectively diverted either to the collect bag 38 or to the return reservoir 88. In one process for which the disclosed apparatus is particularly useful, excess white blood cells are removed from the donor's blood for therapeutic purposes. The white blood cells and any plasma in which the white blood cells may be suspended may be discarded, with the intention that the donor's white cell count be lowered to an acceptable level. The quantity of fluid withdrawn from the donor for disposal or collection is known from the size of the loop 108 and from the number of revolutions of the peristaltic pump 126.

A second collection pump 128 is coupled to the plasma line 64 at loop 100. The second collection pump 128 draws liquid and particles from the cell separation vessel 12. Beyond pump 128, loop 100 again divides into the two lines 104, 96. The valve 101 on the device 6 selectively opens and closes the lines. Line 104 is coupled to the reservoir 88 and ordinarily returns plasma to the donor. Line 96 is coupled to needles or connectors 98 that allow replacement fluid to flow by gravitational force into the reservoir 88. Both the plasma line 64 and the line 94 are open and blood processing continues while replacement fluid is added. The quantity of plasma being returned to the donor is known from the size of loop 100 and the number of revolutions of peristaltic collect pump 128. The amount of replacement fluid added through line 96 is not measured by the action of a pump in contact with line 96.

Any fluids collected in the reservoir 88 are returned to the donor by the action of return pump 127, which engages loop 90 in return line 72. The amount of fluids returned to the donor is known from the size of loop 90 and the number of revolutions of return pump 127.

The volume of whole blood being removed from the donor together with added AC is therefore known directly from the inlet pump 124. The amount of AC being added to the donor's blood is known from AC pump 125. Similarly, the total volume of fluids being returned to the donor is known from the return pump 127. The amount of plasma being returned is known from pump 128 and the amount of white blood cells (or similar component) being removed for collection or disposal or being returned to the donor is know from pump 126. It is important, however, to control the amount and rate of delivery of replacement fluid added to the donor's blood to maintain a healthy fluid balance in the donor. In the apparatus shown, a pump is not available that can be dedicated to the control of replacement fluid. Replacement fluid is introduced into the disposable system by gravitational force alone. The quantity of replacement fluid is determined and controlled in the following manner.

Either plasma or replacement fluid or both are supplied to the reservoir 88 through return loop 104, depending on the orientation of the valve 101. In addition, flow may be completely interrupted by stopping the plasma pump 128 and closing the replacement fluid line 96 with valve 101. Red blood cells ordinarily also flow into the return reservoir 88, unless the inlet pump 124 is stopped. In any case, as pointed out above, the quantity of red blood cells entering the return reservoir can be known from the status of the inlet pump less the plasma pump 128 and the white blood cell pump 126. The return reservoir repeatedly fills with fluid and empties fluid into the return line 72. A lower sensor (not shown) in contact with the reserve reservoir 88 senses a level of fluid in the return reservoir 88. A cycle is considered to be a period when the fluid level rises above the lower sensor until the fluid level returns to the lower sensor. Each cycle represents a quantity of fluid removed from the return reservoir by the return pump 127 and returned to the donor. An upper sensor (not shown) may also be provided, which is also in contact with the reserve reservoir and which is used to detect an excessive rise of the fluid level in the return reservoir. If the fluid level reaches the upper sensor, flow rates into or out of the reservoir would be adjusted to lower the fluid level. It is preferred that each cycle comprise several revolutions of the return pump 127. Moreover, replacement fluid is added to the return reservoir 88 only in alternate cycles and preferably only in one in every four cycles (one cycle with replacement fluid to three cycles without replacement fluid) or one in every five cycles (one cycle with replacement fluid to four cycles without replacement fluid). These ratios allow sufficiently accurate control of the amount of replacement fluid being administered to the donor. Because the inflow into the return reservoir 88 from red blood cells (pump 124 less pump 128 and pump 126), from plasma (pump 128), and from white blood cells (pump 126 or valve 121) are known and because the outflow from the return reservoir 88 is known (return pump 127), the remaining inflow from the gravity-fed replacement fluid line 96 can be calculated. The amount of replacement fluid returned to the donor can, therefore, be kept within safe limits, despite the fact that a dedicated pump, capable of directly measuring the inflow of replacement fluid, is not available.

Blood within the processing vessel 12 is subjected to centrifugal force causing components of the blood components to separate. The components of whole blood stratify in order of decreasing density as follows: (1) red blood cells, (2) white blood cells, (3) platelets, and (4) plasma. The controller regulates the rotational speed of the centrifuge channel assembly 16 to ensure that this particle stratification takes place. A layer of red blood cells (high density components) forms along the outer wall of the processing vessel 12 and a layer of plasma (lower density components) forms along the inner wall of the processing vessel 12. Between these two layers, the intermediate density platelets and white blood cells (intermediate density components) form a buffy coat layer. Preferably, the separation is observed in two dimensions by a camera and controlled as described in U.S. Pat. No. 7,422,693, which is incorporated herein by reference.

Figure 4:
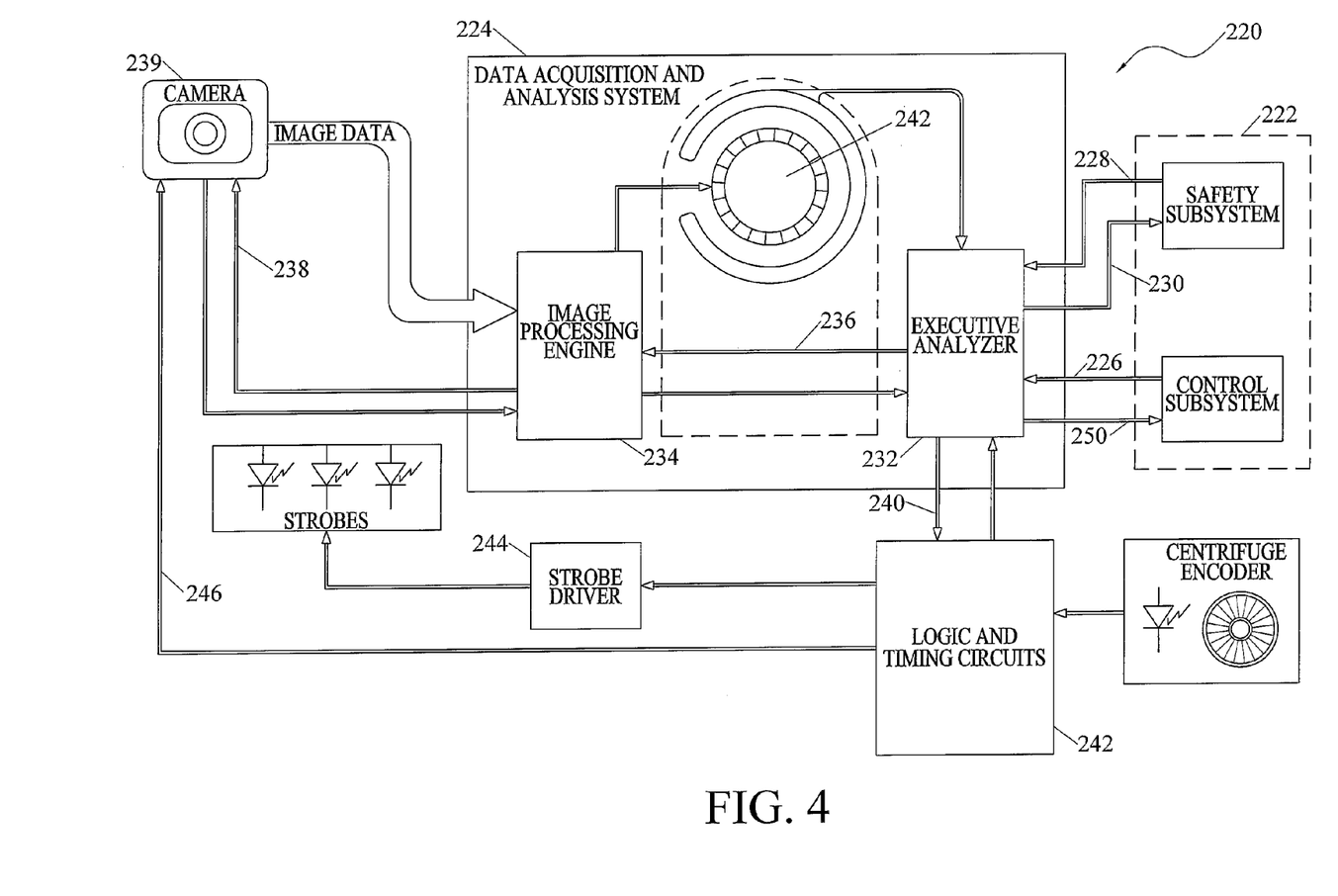
FIG. 4 is a schematic diagram of a camera-controlled apheresis system.

FIG. 4 shows a schematic of a process control system for the blood processing device 6. The exemplary control system 220 illustrated in FIG. 4 comprises master Procedure Control system 222 in two way communication with a data acquisition and analysis system 224. Master Procedure Control system 222 is capable of receiving input signals corresponding to a selected blood processing procedure, a sample undergoing processing, or a patient undergoing treatment. Based on these input signals, Procedure Control System 222 generates and transmits procedure requests and procedure commands 226 to the smart slave data acquisition and analysis system 224. The master Procedure Control system 222 also generates and transmits a series of test commands 228 to smart slave data acquisition and analysis system 224. Data acquisition and analysis system 224 is capable of receiving test commands 228 and generating test response signals 130 which verify that the control system 120 is fully functional and that the patient or blood sample identified by the data acquisition and analysis system 224 is correctly associated with the selected blood processing procedure or therapy.

The data acquisition and analysis system 224 comprises a first computer processor 232 in two-way communication with a second computer processor 234. First computer processor 232 is configured to receive procedure requests and procedure commands 226 from master Procedure Control system 222 and transmit processing commands 236 to second computer processor 234. Second computer processor 234 analyzes the processing commands 236 and transmits camera setting commands 238 to a CCD camera and light collection element 239 which provide information related to establishing the proper exposure time, camera and light collection element position, field of view, color or monochrome imaging and other parameters necessary for acquiring high quality images of the blood processing device. First computer processor 232 is also configured to transmit illumination control and triggering commands 240 to light source and camera triggering hardware 242. Using centrifuge positional encoder data, the triggering hardware 242 transmits electronic trigger signals to light source driver circuits 244 and camera trigger 246. Camera 239 measures light intensities comprising images of the observation region on the blood processing device 6. The raw image data is transmitted to the second computer processor 234 for image formatting and real time image processing. In a density centrifuge, an image is acquired upon every second rotation of the separation chamber. For a rotational velocity of 3000 rotations per minute, this corresponds to acquisition of an image every 40 milliseconds. At low rotational velocities, an image may be acquired on every rotation of the separation chamber. The formatted image data is operated on by second computer processor 234 using one or more image-processing algorithms, which extract measurements from the image data and determine information about physical and chemical characteristics of the blood components undergoing processing and the operation of the blood processing device itself.

Immediately after creation of a new image data object, it is placed onto a linked list of image data objects designated as the image data list 242. This list stores image data information backwards in time. For an acquisition rate of 25 frames per second, 25 image data objects are inserted onto the image data list every second. The image data list acts as a managed circular buffer by deleting the oldest image data off the tail end of the list while inserting newly acquired image date at the head of the list.

Image data objects in the image data list are periodically examined by the first computer processor 232 and provide key data sets for monitoring and controlling blood processing. Measurements generated from the operation of the image-data analysis algorithms establish the basis of image information output signals 250 sent to the master Procedure Control system 222 and also serve as the basis of output signals sent to the camera 239, light sources, and camera trigger 246 to optimize the quality of the images acquired an analyzed.

Centrifugation device controllers are capable of selective adjustment of the position of one or more phase boundaries along the separation axes. For example, centrifugation device controllers may adjust the position of phase boundaries by varying the flow rates of one or more selected blood components out of the separation chamber. This can be achieved through the use of pumps, such as peristaltic pumps described above, to effectuate fluid flow through tubing. The centrifuge controller is capable of regulating the infusion of a blood agent, such as an anti-coagulating agent, to the blood sample undergoing processing, of causing the removal of a selected component such as white blood cells, and of adding a controlled quantity of replacement solution, as described above. As described herein, the quantity of replacement fluid can be controlled without a dedicated peristaltic pump, by control of fluid inflows and out flows in the manner described above.

Although the inventive device and method have been described in terms of filtering white blood cells, this description is not to be construed as a limitation on the scope of the invention. It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

What is claimed is:

1. A method of providing a controlled amount of blood replacement fluid to a blood donor comprising:
   providing a disposable blood processing set for use on a centrifugal blood processing device, said disposable set comprising:
   a blood separation chamber adapted to be mounted on a rotor of said centrifugal blood processing device;
   a blood inlet line adapted to be coupled to a blood donor and to an inlet pump on said centrifugal blood processing device;
   an anti-coagulant line in fluid communication with said inlet line, said anti-coagulant line being adapted to be fluidly coupled to a supply of anti-coagulant and being further adapted to be coupled to an anti-coagulant pump on said centrifugal blood processing device;
   a reservoir adapted to be coupled to at least one sensor for detecting a level of fluid in said reservoir; a return line in fluid communication with said reservoir, said return line being adapted to be coupled to said blood donor and to a return pump on said centrifugal blood processing device;
   a red blood cell line in fluid communication with said blood separation chamber and said reservoir;
   a collect line in fluid communication with said blood separation chamber and in selective communication with said reservoir and a collect bag, said collect line being adapted to be coupled to a collect pump;
   a plasma line in fluid communication with said blood separation chamber and with said reservoir, said plasma line being adapted to be coupled to a plasma pump; and
   a replacement fluid line in fluid communication with said reservoir and adapted to be placed in fluid communication with a source of replacement fluid;

mounting said disposable blood processing set on said centrifugal blood processing device;

removing whole blood from said donor through said inlet line;

providing anti-coagulant to said whole blood in said inlet line;

measuring the flow of said whole blood and said anti-coagulant in said inlet line;

separating said whole blood and said anti-coagulant into a plurality of blood components in said separation chamber;

flowing red blood cells from said separation chamber into said reservoir;

flowing a first blood component from said separation chamber into said reservoir;

measuring the flow of said first blood component into said reservoir;

removing a second blood component from said separation chamber;

measuring the flow of said second component;

selectively flowing at least part of said second component into said reservoir;

selectively flowing replacement fluid into said reservoir;

periodically flowing contents of said reservoir into said return line;

measuring the flow of said contents;

determining a quantity of replacement fluid delivered to said donor from said measured inlet line flow, first blood component flow, collect flow and return flow.

2. The method of claim 1 wherein the step of selectively flowing replacement fluid into said reservoir comprises allowing said replacement fluid to flow without mechanical assistance.

3. The method of claim 2 wherein said replacement fluid flows by gravitational force alone.

4. The method of claim 1 wherein the step of measuring the flow of said contents comprises counting revolutions of a peristaltic pump.

5. The method of claim 1 wherein said step of periodically flowing contents of said reservoir into said return line further comprises flowing the contents of said reservoir during a first period of time when replacement fluid is not flowed into said reservoir and flowing the contents of said reservoir during a second period of time when replacement fluid is flowed into said reservoir.

6. The method of claim 5 wherein said first and second periods of time alternate.

7. The method of claim 6 wherein said first period is at least as long as said second period.

8. The method of claim 5 wherein each of said periods comprise at least one cycle, each cycle comprising a discrete step of removing whole blood and a discrete step of flowing contents of the reservoir into the return line.

9. The method of claim 8 wherein the ratio of the number of cycles in said first period to the number of cycles in said second period is at least 1 to 1.

\* \* \* \* \*